United States Patent [19]
Lundstrom et al.

[11] Patent Number: 5,469,856
[45] Date of Patent: Nov. 28, 1995

[54] METHOD AND DEVICE FOR FILTERING OUT BASELINE FLUCTUATIONS FROM AN ELECTROCARDIOGRAM

[75] Inventors: Lena Lundstrom; Peter Karlsson, both of Stockholm; Thomas Ohlsson, Vallingby, all of Sweden

[73] Assignee: Siemens Aktiengesellschaft, Munich, Germany

[21] Appl. No.: 117,069

[22] PCT Filed: Mar. 4, 1992

[86] PCT No.: PCT/EP92/00473

§ 371 Date: Dec. 22, 1993

§ 102(e) Date: Dec. 22, 1993

[87] PCT Pub. No.: WO92/15242

PCT Pub. Date: Sep. 17, 1992

[30] Foreign Application Priority Data

Mar. 4, 1991 [DE] Germany .......................... 41 06 856.4

[51] Int. Cl.[6] ......................................................... A61B 5/04
[52] U.S. Cl. ........................................................... 128/696
[58] Field of Search ..................................... 128/695, 696, 128/706, 710, 901, 703, 708, 902

[56] References Cited

U.S. PATENT DOCUMENTS

| | | | |
|---|---|---|---|
| 4,261,369 | 4/1981 | Allor | 128/696 |
| 4,281,664 | 8/1981 | Duggan | 128/696 |
| 5,016,642 | 5/1991 | Dukes et al. | 128/696 |
| 5,074,303 | 12/1991 | Hauck | 607/17 |
| 5,259,387 | 11/1993 | dePinto | 128/696 |

Primary Examiner—William E. Kamm
Assistant Examiner—Jeffrey R. Jastrzab
Attorney, Agent, or Firm—Hill, Steadman & Simpson

[57] ABSTRACT

Method and device for filtering out baseline fluctuations from an electrocardiogram. It is known to provide a high pass filter for filtering out baseline fluctuations from an electrocardiogram, the lower cut off frequency of a high pass filter is at a value below the frequencies which are characteristic of the heart signals at the lowest possible heart rate. In order to increase the effectiveness of the baseline filtering, it is provided that in a device (4) the current heartbeat rate is determined from the electrocardiogram and, in dependence thereupon, the lower cut off frequency of the filter (2) is altered in such a manner that the lower cut off frequency is increased in the case of an increasing heartbeat rate and is decreased in the case of a decreasing heartbeat rate.

5 Claims, 1 Drawing Sheet

METHOD AND DEVICE FOR FILTERING OUT BASELINE FLUCTUATIONS FROM AN ELECTROCARDIOGRAM

BACKGROUND OF THE INVENTION

1. Field of the Invention

The invention relates generally to a method and a device for filtering out baseline fluctuations from an electrocardiogram by means of a high pass or band pass filter.

2. Description of the Related Art

Electrocardiograms derived from patients are normally overlaid by disturbance signals such as, for example, the 50 Hz (60 Hz in the United States) alternating voltage induced by the alternating current grid, electrical muscle potentials and artifacts resulting from taking the electrocardiogram from the patient. To the extent that these disturbances are of low-frequency type in comparison with the heartbeat rate, they are expressed in the form of baseline fluctuations in the respectively recorded electrocardiogram.

It is known for example from "Journal of Clinical Engineering", Volume 7, No. 3, July–September 1982, pages 235–240, to filter out these baseline fluctuations from the recorded electrocardiogram by means of a high pass filter. In this case, the lower cut off frequency of the high pass filter is set to a value which is below the frequencies which are characteristic of the heart signals at the lowest occurring heart rate. At high heartbeat rates, there is therefore a disturbance frequency range which is not covered by the high pass filtering.

SUMMARY OF THE INVENTION

It is an object of the present invention to improve the effectiveness of the baseline filtering of an electrocardiogram signal.

The above object is inventively achieved in a method having the steps of determining the current heartbeat rate from the electrocardiogram signal taken from the patient and altering the lower cut off frequency depending on the current heartbeat rate. The lower cut off frequency is increasingly altered in the case of an increasing heartbeat rate and decreasingly altered in the case of a decreasing heartbeat rate.

The above object is inventively achieved in an apparatus for filtering out baseline fluctuations from an electrocardiogram signal having a high pass or band pass filter with a variable low cut off frequency. The input of the filter, which is acted upon by the electrocardiogram signal connects with the input of a device for determining the heartbeat rate from the electrocardiogram signal. This device connects on the output side with a control output of the filter to control the lower cut off frequency.

An advantage of the method of the present invention or of the apparatus the present invention is the matching of the lower cut off frequency of the filter to the determined heartbeat rate whereby the maximum possible component of the baseline fluctuations is continuously filtered out from the electrocardiogram signal.

The determination of the heartbeat rate advantageously occurs by subjecting the electrocardiogram signal to a frequency analysis, or an alternative thereto. Such frequency analysis can be performed by using a frequency analyzer. In doing so, component frequencies in the electrocardiogram signal are determined and the lowest "useful" component can be fixed and used to determine the lower cut-off frequency of the filter. The components below the cut-off frequency are in the unwanted baseline fluctuations and are thus filtered out. In an alternative embodiment, a QRS detector, a downstream stage and a reciprocal value former are used. A largest period in the "useful" electrocardiogram signal is determined by measuring the temporal spacing of the detected QRS complexes with the downstream stage. The reciprocal value from the reciprocal value former forms the lower cut-off frequency by taking the reciprocal value of the period. The occurrence of QRS complexes in the electrocardiogram signal is detected and the reciprocal value is thus formed from the temporal spacing of successive, detected QRS complexes.

BRIEF DESCRIPTION OF THE DRAWING

The exemplary embodiments of the method and apparatus for filtering out baseline fluctuations from an electrocardiogram signal of the present invention shall be set forth in greater detail below with reference to the figures.

DESCRIPTION OF THE PREFERRED EMBODIMENTS

Figure 1:
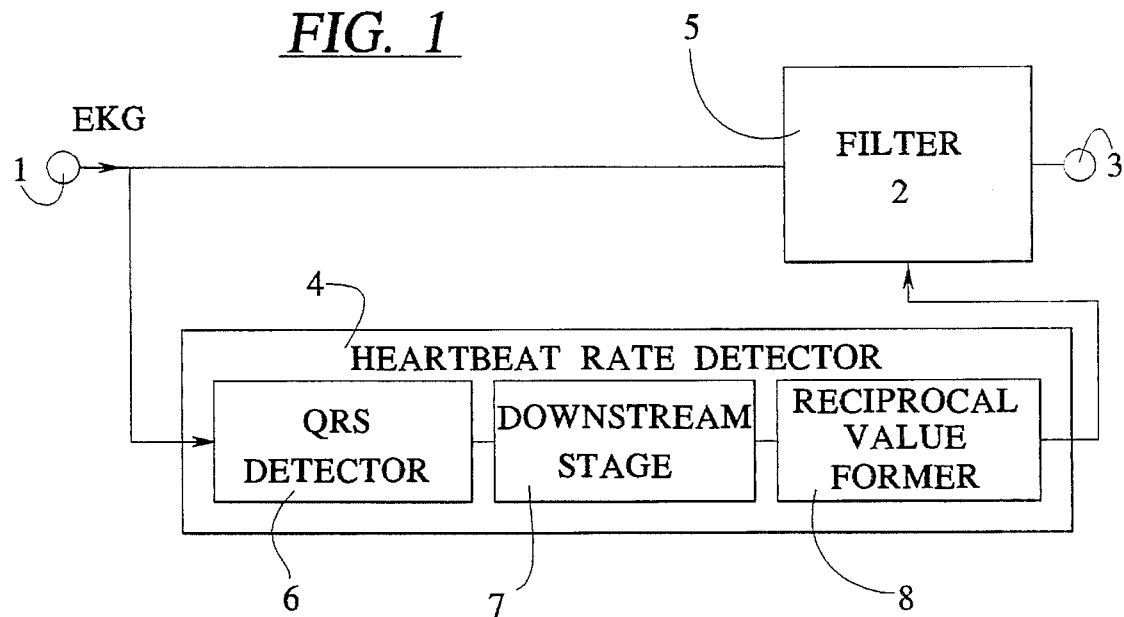
FIG. 1 shows a block diagram of an illustrative embodiment of the apparatus of the present invention.
Figure 2:
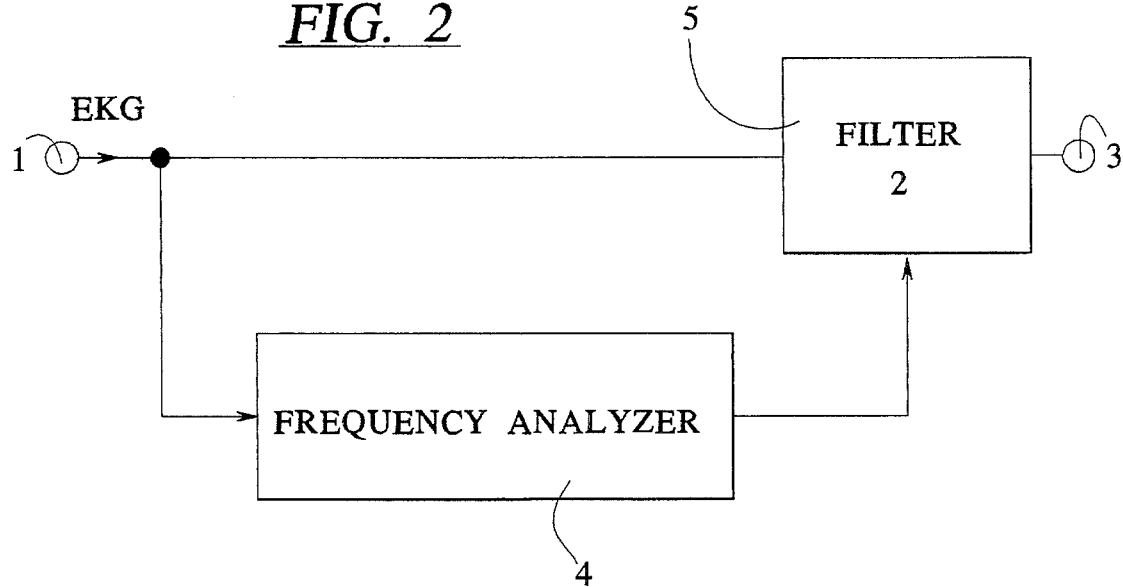
FIG. 2 shows a block diagram of another illustrative embodiment of the apparatus of the present invention.

In FIG. 1, reference symbol 1 designates a connection at which an electrocardiogram is taken from a patient (not shown). The connection 1 connects with the input of a high pass or band pass filter 2, at the output 3 of which the electrocardiogram, which is filtered and thus cleared of baseline fluctuations, can be taken. The connection 1 further connects with the input of a device for determining the heartbeat rate from the electrocardiogram. The output of this device 4 connects with a control input 5 of the filter 2 for controlling the lower cut off frequency of the filter 2. In the case of the illustrative embodiment shown in FIG. 1, the device 4 includes a QRS detector 6, which detects the occurrence of QRS complexes in the electrocardiogram. A downstream stage 7 for the measurement of the temporal spacing between successive detected QRS complexes and a reciprocal value former 8, connects thereto to form the reciprocal value from the determined temporal spacing. By way of an alternative to the illustrative embodiment shown in FIG. 1, the device 4 can also comprise a frequency analyzer as illustrated in FIG. 2. The frequency analyzer is similarly connected with its input connected to connection 1 and its output connected to the control input 5 of the filter 2. The frequency analyzer can thus control the lower cut-off frequency of the filter 2 as described above.

As for the filter 2, consideration may be given in particular to digital filters with a settable lower cut off frequency or a series of a plurality of filters with differing fixed cut off frequencies, from which in each instance one filter is selected in dependence upon the output signal of the device 4. High pass or band pass filters, frequency analyzers and QRS detectors are known per se, so that a more detailed description is not required.

Although various modifications may be suggested by those versed in the art, it should be understood that I wish to embody within the scope of the patent granted hereon, all such modifications as reasonably and properly come within the scope of my contribution to the art.

We claim:

1. A method for filtering out baseline fluctuations from an electrocardiogram, comprising the steps of:

determining a current heartbeat rate from said electrocardiogram by subjecting said electrocardiogram to a frequency analysis;

filtering said electrocardiogram in a filter having a lower cut off frequency; and altering said lower cut off frequency of said filter, by increasing said lower cut off frequency in the presence of an increasing heartbeat rate and decreasing said lower cut off frequency in the presence of a decreasing heartbeat rate.

2. An apparatus for filtering out baseline fluctuations from an electrocardiogram signal comprising:

a bandpass filter having a signal input, a variable lower cut off frequency, a control input and an output, said electrocardiogram signal being supplied to said signal input; and means connected to said signal input of said filter for determining a heartbeat rate from said electrocardiogram signal, said heartbeat rate being supplied to said control input of said filter for varying said lower cut off frequency dependent on said heartbeat rate.

3. A method for filtering out baseline fluctuations from an electrocardiogram, the method comprising the steps of:

filtering said electrocardiogram in a filter having a lower cut off frequency;

determining a current heartbeat rate from said electrocardiogram by detecting occurrences of QRS complexes having a temporal spacing therebetween in said electrocardiogram; and forming a reciprocal value from the temporal spacing of successive, detected QRS complexes and altering said lower cut off frequency of said filter dependent on said heartbeat rate.

4. An apparatus for filtering out baseline fluctuations from an electrocardiogram signal comprising:

a filter having a signal input, a variable lower cut off frequency, a control input and an output, said electrocardiogram signal being supplied to said signal input; and a frequency analyzer capable of determining a heartbeat rate from said electrocardiogram signal, said frequency analyzer connected to said signal input of said filter, said heartbeat rate being supplied to said control input of said filter for varying said lower cut off frequency dependent on said heartbeat rate.

5. An apparatus for filtering out baseline fluctuations from an electrocardiogram signal comprising:

a filter having a signal input, a variable lower cut off frequency, a control input and an output, said electrocardiogram signal being supplied to said signal input;

a QRS detector connected to said signal input of said filter to determine a heartbeat rate from said electrocardiogram signal, said QRS detector having an output;

measurement means connected to said output of said QRS detector for measuring chronological spacing between successive, detected QRS complexes, said measurement means having an output; and means connected to said output of said measurement means for forming a reciprocal of said chronological spacing indicative of said heartbeat rate, said heartbeat rate being supplied to said control input of said filter for varying said variable lower cut-off frequency dependent on said heartbeat rate.

* * * * *